(12) United States Patent
Suto et al.

(10) Patent No.: US 9,901,101 B2
(45) Date of Patent: Feb. 27, 2018

(54) METHOD FOR SELECTIVELY INHIBITING SULFATE-REDUCING BACTERIUM, GYPSUM COMPOSITION CAPABLE OF INHIBITING PROLIFERATION OF SULFATE-REDUCING BACTERIUM BY SAID METHOD, GYPSUM-TYPE SOLIDIFYING MATERIAL, AND GYPSUM-TYPE BUILDING MATERIAL

(71) Applicant: YOSHINO GYPSUM CO., LTD., Tokyo (JP)

(72) Inventors: Koichi Suto, Sendai (JP); Chihiro Inoue, Sendai (JP); Masato Yamaguchi, Tokyo (JP); Shinichi Miura, Tokyo (JP)

(73) Assignee: YOSHINO GYPSUM CO., LTD., Tokyo (JP)

( * ) Notice: Subject to any disclaimer, the term of this patent is extended or adjusted under 35 U.S.C. 154(b) by 259 days.

(21) Appl. No.: 14/421,359

(22) PCT Filed: Aug. 9, 2013

(86) PCT No.: PCT/JP2013/071612
§ 371 (c)(1),
(2) Date: Feb. 12, 2015

(87) PCT Pub. No.: WO2014/027613
PCT Pub. Date: Feb. 20, 2014

(65) Prior Publication Data
US 2015/0216177 A1    Aug. 6, 2015

(30) Foreign Application Priority Data

Aug. 15, 2012 (JP) .................. 2012-180093
Aug. 15, 2012 (JP) .................. 2012-180094

(51) Int. Cl.
*C04B 28/14* (2006.01)
*A01N 59/06* (2006.01)
*C04B 111/20* (2006.01)

(52) U.S. Cl.
CPC ............. *A01N 59/06* (2013.01); *C04B 28/14* (2013.01); *C04B 28/144* (2013.01); *C04B 2111/2092* (2013.01)

(58) Field of Classification Search
CPC .............. C04B 28/14; C04B 28/144; C04B 2111/2092; A01N 59/06
USPC ................ 424/682, 685, 690, 691; 106/772; 504/120
See application file for complete search history.

(56) References Cited

U.S. PATENT DOCUMENTS 4,724,242 A   2/1988  Vassileff
5,817,262 A   10/1998 Englert 5,980,628 A       11/1999  Hjelmeland et al.
6,352,585 B1      3/2002   Diesso
6,514,327 B1      2/2003   Burge et al.
2002/0124773 A1   9/2002   Diesso
2009/0214606 A1   8/2009   Bujard et al.
2012/0178849 A1   7/2012   Yamashita

FOREIGN PATENT DOCUMENTS

| JP | 61-127656 | 6/1986 |
|---|---|---|
| JP | H0733503 | 2/1995 |
| JP | 98/028240 | 7/1998 |
| JP | 11-21160 | 1/1999 |
| JP | 2000-505775 | 5/2000 |
| JP | 2001180994 | 7/2001 |
| JP | 2002-001397 | 1/2002 |
| JP | 2002-177992 | 6/2002 |
| JP | 2002177992 A * | 6/2002 |
| JP | 2004-329757 | 11/2004 |
| JP | 2010-208870 | 9/2010 |
| JP | 2011088824 | 5/2011 |
| JP | 4695254 | 6/2011 |
| WO | 9733477 | 9/1997 |
| WO | 2011105396 | 9/2011 |

OTHER PUBLICATIONS

Amonette et al.: "Toxicity of Al to *Desulfovibrio desulfuricans*"; Applied and Environmental Microbiology, Jul. 2003, vol. 69, No. 7, pp. 4057-4066.
Suto et al.: "Examination of a new reduction bacteria restraint technique aiming at reuse promotion of the abolished gypsum sulfate"; The Mining and Materials Processing Institute of Japan Shunki Taikai Koenshu, 2013, pp. 305-306, No. 3203 with an English abstract.
Extended European Search Report, issued in the corresponding European patent application No. 13879516.6, dated May 13, 2016, 14 pages.
Supplementary Partial European Search Report, issued in the corresponding European patent application No. 13879516.6, dated Jan. 22, 2016, 10 pages.
Gershon et al., "Antimicrobal Activity of Metal Chelates of Salts of 8-Quinolinols with Aromatic Hydroxycarboxylic Acids", Activity of Metal Chelate Complexes, vol. 10, pp. 556-560, Jun. 6, 1962.
Korean Office Action, issued in the corresponding Korean patent application No. 10-2015-7005067, dated Nov. 19, 2015, 5 pages.
Japanese Office Action, issued in the corresponding Japanese Patent Application No. 2012-180094, dated Feb. 9, 2016, 12 pages.

(Continued)

*Primary Examiner* — Helene Klemanski
(74) *Attorney, Agent, or Firm* — Hamre, Schumann, Mueller & Larson, P.C.

(57) ABSTRACT

A method for performing selective bacteriostasis of a sulfate-reducing bacterium, the method selectively inhibiting proliferation of the sulfate-reducing bacterium by allowing chelated Al to coexist in an environment where the sulfate-reducing bacterium exists, and a gypsum composition containing calcined gypsum (A) and chelated Al (B), in which the chelated Al (B) is contained in a range of 0.01 to 20 mass parts relative to 100 mass parts of the calcined gypsum (A).

6 Claims, 3 Drawing Sheets

(56) References Cited

OTHER PUBLICATIONS

Australian Office Action, issued in the corresponding Australian patent application No. 2013303570, dated Apr. 13, 2015, 3 pages.
European Office Action, issued in the corresponding European patent application No. 13 879 516.6 dated Apr. 6, 2017, 10 pages.
Lee et al., "Calcium-chelating alizarin and other anthraquinones inhibit biofilm formation and the hemolytic activity of *Staphylococcus aureus*", Scientific Reports, Jan. 14, 2016, pp. 1-11.
Tiedemann et al., "Fiber—safe Extraction of Red Mordant Dyes from Hair Fibers", Journal of the American Institute for Conservation, vol. 34, No. 3, Article 4, 1995, 3 pages.
Puchtler et al., "On the History and Mechanism of Alizarin and Alizarin Red S Stains for Calcium", The Journal of Histochemistry and Cytochemistry, vol. 17, No. 2, 1969, pp. 110-124.
Kiel et al., "Metal Complexes of Alizarin I—The Structure of the Calcium-Aluminium Lake of Alizarin", Society of Dyers and Colourists/Coloration Technology, vol. 79, issue 1, Jan. 1963, pp. 21-27.

* cited by examiner

메THOD FOR SELECTIVELY INHIBITING SULFATE-REDUCING BACTERIUM, GYPSUM COMPOSITION CAPABLE OF INHIBITING PROLIFERATION OF SULFATE-REDUCING BACTERIUM BY SAID METHOD, GYPSUM-TYPE SOLIDIFYING MATERIAL, AND GYPSUM-TYPE BUILDING MATERIAL

TECHNICAL FIELD

The present invention relates to a method for performing selectively bacteriostasis of a sulfate-reducing bacterium, the method only inhibiting the proliferation of the sulfate-reducing bacterium without inhibiting the proliferation of other bacteria. The present invention also relates to a gypsum composition, a gypsum-based solidifying material, and a gypsum-based building material capable of inhibiting generation of hydrogen sulfide a sulfur source of which is gypsum.

BACKGROUND ART

A sulfate-reducing bacterium is a bacterium that oxidizes an organic substance with a sulfate ion as an electron acceptor to acquire energy. The growth temperature range of the sulfate-reducing bacterium is different depending on the kind thereof, and thermophilic bacteria, mesophilic bacteria, psychrotrophic bacteria, and psychrophilic bacteria are present. Moreover, depending on the difference in growth pH, bacteria that grow well around a neutral pH range and bacteria that grow well under an acidic or alkaline condition are present. Moreover, their living areas cover a wide range such as the inside of see mud, general soil, hot water-spurting areas, pipe lines, and so on.

In the process of acquiring energy of the sulfate-reducing bacterium, hydrogen sulfide as a reductant of a sulfate ion is produced. The hydrogen sulfide is a substance that has strong toxicity and corrosiveness and emits offensive odor, and therefore a problem arises when a large amount of hydrogen sulfide is produced. For example, hydrogen sulfide is generated when the sulfate-reducing bacterium acquires energy making use of a sulfate ion as an electron acceptor that is contained in natural water, fertilizers (ammonium sulfate and so on), or the like and problems that the generated hydrogen sulfide inhibits the growth of crops in agricultural fields and corrodes ion materials (underground pipes and so on) have been known.

Moreover, the generation of hydrogen sulfide a sulfur source of which is illegally dumped gypsum has become a problem in recent years. It is known that the hydrogen sulfide generation is associated with the sulfate-reducing bacterium.

The hydrogen sulfide generation from a waste gypsum plasterboard has been reported as an example of the hydrogen sulfide generation due to the sulfate-reducing bacterium. The waste gypsum plasterboard contains paste and paper (nutrients) in addition to calcium sulfate (sulfate ion) that is a main component. Accordingly, it sometimes occurs that the sulfate-reducing bacterium in soil assimilates the waste gypsum plasterboard resulting in hydrogen sulfide generation.

Thus, attempts have been made to inhibit the proliferation of the sulfate-reducing bacterium to thereby suppress the hydrogen sulfide production. For example, the present applicant has disclosed a method for inhibiting proliferation of a sulfate-reducing bacterium to thereby suppress hydrogen sulfide generation by adding an anthraquinone compound to a soil-treating material that contains gypsum as a main component (see, Patent Literature 1).

However, since the anthraquinone compound that is extremely expensive is used in the technology described in Patent Literature 1, there has been a problem in terms of production cost. The actual circumstance is that the utilization of the technology has not widely been spread with the cost being an obstacle particularly in applications such as a soil-treating material where a large amount of anthraquinone compound is used.

Thus the present applicant has also disclosed a method for inhibiting proliferation of a sulfate-reducing bacterium to thereby suppress the hydrogen sulfide generation by adding a specified aluminum compound such as a hydrate of aluminum sulfate $[Al_2(SO_4)_3 \cdot nH_2O$ (n=6, 10, 16, 18, or 27] to a gypsum composition (see, Patent Literature 2).

CITATION LIST

Patent Literature

Patent Literature 1: Japanese Patent Laid-Open No. 2002-177992 Patent Literature 2: Japanese Patent Laid-Open No. 2010-208870

SUMMARY OF INVENTION

Technical Problem

Since the aluminum compound that is inexpensive and readily available as compared with the anthraquinone compounds is used in the method described in Patent Literature 2, the method described in Patent Literature 2 can solve the problem of production cost that the technology described in Patent Literature 1 faces. However, there has still been some room for improvement regarding the following item in the technology described in Patent Literature 2.

Namely, although it is possible to inhibit the proliferation of the sulfate-reducing bacterium to thereby suppress the hydrogen sulfide production according to the method described in Patent Literature 2, there has sometimes been a case that the proliferation of a bacterium other than the sulfate-reducing bacterium (hereinafter, referred to as "another bacterium") is inhibited. When the proliferation of another bacterium is inhibited, microorganism phases in soil or the like are destroyed and there sometimes occurs a problem such as offensive odor emission or plant growth disorders. Accordingly, it has earnestly been desired to establish a method that is capable of selectively inhibiting the proliferation of the sulfate-reducing bacterium without inhibiting the proliferation of another bacterium.

The present invention has been made to solve the problems of the conventional technologies. Namely, the present invention intends to provide a method for performing selective bacteriostasis of a sulfate-reducing bacterium, a gypsum composition, a gypsum-based solidifying material, and a gypsum-based building material which are capable of selectively inhibiting the proliferation of the sulfate-reducing bacterium without inhibiting the proliferation of another bacterium.

Solution to Problem

The present inventors have made diligent studies on the problems to find out that chelated Al has a function of selectively inhibiting the proliferation of the sulfate-reducing bacterium, and have completed the present invention.

[1] Method for Performing Selective Bacteriostasis of Sulfate-Reducing Bacterium:

Namely, according to the present invention, a method for performing selective bacteriostasis of a sulfate-reducing bacterium, the method selectively inhibiting proliferation of the sulfate-reducing bacterium by allowing chelated Al to coexist in an environment where the sulfate-reducing bacterium exists.

It is preferable in the method of the present invention to produce the chelated Al in the environment where the sulfate-reducing bacterium exists by adding an $Al^{3+}$ source and a chelating agent to the environment. Moreover, it is preferable in the method of the present invention that the $Al^{3+}$ source is at least one aluminum compound selected from the group consisting of $Al_2O_3$, $AlCl_3$, $Al(OH)_3$, and $Al_2(SO_4)_3$. Furthermore, it is preferable in the method of the present invention that the sulfate-reducing bacterium is a bacterium that lives in a middle temperature range (20 to 45° C.) and a neutral range (a pH of 5 to 9).

[2] Gypsum Composition:

Moreover, according to the present invention, a gypsum-based composition comprising gypsum (A) and chelated Al (B), wherein the chelated Al (B) is contained in a range of 0.01 to 20 mass parts relative to 100 mass parts of the gypsum (A) is provided.

It is preferable in the composition of the present invention that an $Al^{3+}$ source (b-1) and a chelating agent (b-2) are contained in place of the chelated Al (B). Moreover, it is preferable in the composition of the present invention that the $Al^{3+}$ source (b-1) is at least one Al compound selected from the group consisting of $Al_2O_3$, $AlCl_3$, $Al(OH)_3$, and $Al_2(SO_4)_3$.

It is preferable in the composition of the present invention that a part or the whole of the gypsum is waste gypsum, and it is preferable in the composition of the present invention that a part or the whole of the gypsum is calcined gypsum.

[3] Gypsum-Based Solidifying Material and Gypsum-Based Building Material:

Furthermore, according to the present invention, a gypsum-based solidifying material comprising the gypsum composition in which a part or the whole of the gypsum is calcined gypsum is provided. Moreover, according to the present invention, a gypsum-based building material obtained by adding water to the gypsum composition in which a part or the whole of the gypsum is calcined gypsum, and molding and solidifying the gypsum composition is provided.

Advantageous Effects of Invention

The selective bacteriostasis method, the gypsum composition, and so on of the present invention can selectively inhibit the proliferation of a sulfate-reducing bacterium. Accordingly the selective bacteriostasis method, the gypsum composition, and so on of the present invention can inhibit the proliferation of the sulfate-reducing bacterium to thereby suppress the hydrogen sulfide production. On the other hand, with the selective bacteriostasis method, the gypsum composition, and so on of the present invention, the proliferation of another bacterium is not inhibited, and therefore a microorganism phases in soil are not destroyed and there is no risk of causing a problem such as offensive odor emission or plant growth disorders to occur.

DESCRIPTION OF EMBODIMENTS

Hereinafter, the present invention will be described in detail. However, the present invention is not limited by the following embodiments and includes all objects having matters used to specify the invention.

[1] Method for Performing Selective Bacteriostasis of Sulfate-Reducing Bacterium:

The present invention relates to a method for performing selective bacteriostasis of a sulfate-reducing bacterium, the method selectively inhibiting the proliferation of the sulfate-reducing bacterium.

As described previously, the "sulfate-reducing bacterium" is a bacterium that oxidizes an organic substance with a sulfate ion as an electron acceptor to acquire energy. The bacterium is widely distributed in anaerobic environments such as general soil and sewage sludge. The kind of the sulfate-reducing bacterium to be an application target of the present invention is not particularly limited. For example, the sulfate-reducing bacterium may be Gram-negative bacteria, Gram-positive bacteria, or archaebacteria.

Specifically, sulfate-reducing bacteria such as *Desulfovibrio* (Gram-negative anaerobic bacillus, Gram-negative spirillum), *Desulfuromonas* (Gram-negative anaerobic bacillus, Gram-negative spirillum), *Desulfitobacterium* (Gram-negative strictly anaerobic bacterium), and *Desulfotomaculum* (Gram-positive endospore-forming bacillus) are included.

Specific examples of *Desulfovibrio* bacteria include *Desulfovibrio vulgaris, Desulfovibrio africanus, Desulfovibrio desulfuricans, Desulfovibrio gigas*, and so on. Specific examples of *Desulfotomaculum* bacteria include *Desulfotomaculum ruminis* and so on.

The method of the present invention exhibits the inhibition effect for the whole sulfate-reducing bacteria, namely for any of Gram-negative bacteria, Gram-positive bacteria, and archaebacteria. Among these, the method of the present invention can suitably be used for the sulfate-reducing bacteria that live in the middle temperature range (20 to 45° C.) and the neutral range (a pH of 5 to 9). The aforementioned *Desulfovibrio vulgaris, Desulfovibrio africanus, Desulfovibrio desulfuricans, Desulfovibrio gigas*, and *Desulfotomaculum ruminis* are the "sulfate-reducing bacteria that live in the middle temperature range (20 to 45° C.) and the neutral range (a pH of 5 to 9)".

It is considered that the chelated Al acts to the sulfate-reducing mechanism of the sulfate-reducing bacterium in the method of the present invention to thereby stop the sulfate-reducing mechanism of the sulfate-reducing bacterium and, as a result thereof, selectively inhibits the proliferation of the sulfate-reducing bacterium. The term "selectively" means that the proliferation-inhibiting effect is specific to the sulfate-reducing bacterium. Namely, it means that the proliferation-inhibiting effect for the sulfate-reducing bacterium is recognized but that the proliferation-inhibiting effect for a bacterium other than the sulfate-reducing bacterium (another bacterium) is hardly recognized.

Representative examples of the "another bacterium" include *Escherichia coli* (facultative anaerobic Gram-negative bacillus, Japanese name: Daicho-kin (colon bacillus)), *Clostridium butyricum* (Gram-positive endospore-forming bacillus, Japanese name: Rakusan-kin (butyric acid bacterium)), and so on.

In addition, the term "bacteriostasis" in the present invention means inhibiting the proliferation of a bacterium. Namely, the "bacteriostasis" in the present invention is not required to directly reduce the number of bacteria as in disinfection or sterilization.

[1-1] Chelated Al:

The method of the present invention is characterized in that chelated Al is allowed to coexist in an environment where the sulfate-reducing bacterium exists. The "environment where the sulfate-reducing bacterium exists" is not particularly limited as long as the existence of the sulfate-reducing bacterium can be confirmed. Examples of the environment where the sulfate-reducing bacterium exists include anaerobic environments such as general soil and sewage sludge where sulfate-reducing bacteria are widely distributed. The "chelated Al" denotes a complex that is formed from $Al^{3+}$ and a chelating agent, more specifically a complex in which the chelating agent coordinates with the $Al^{3+}$ that is to be a central ion. The chelated Al is promptly formed by mixing the $Al^{3+}$ source described later and the chelating agent.

The "chelating agent" is a multidentate ligand that coordinates with $Al^{3+}$ to form the chelated Al. In the present invention, the kind of chelating agent is not particularly limited. For example, the chelating agent may be a linear ligand or a cyclic ligand.

Examples of the linear ligand include polycarboxylic acids such as oxalic acid, malonic acid, tartaric acid, glutaric acid, malic acid, citric acid, maleic acid (each of them is a bidentate ligand); polyamines such as ethylene diamine (EDA, bidentate ligand); aminopolycarboxylic acids such as ethylenediaminetetraacetic acid (EDTA, hexadentate ligand); bipyridines such as 2,2'-bipyridine and 1,10-phenathroline (each of them is a bidentate ligand); and so on.

Examples of the cyclic ligand include porphyrins (tetradentate ligands); crown ethers (the coordination number is different depending on the compound. For example, 18-crown-6 is a hexadentate ligand); and so on.

Among the chelating agents, a chelating agent that coordinates with $Al^{3+}$ to readily form chelated Al is preferable. Moreover, since the present invention is often carried out in natural environments, a chelating agent that does not give an adverse effect to the environments is further preferable. Specific examples of the chelating agent include, citric acid, malonic acid, tartaric acid, glutaric acid, malic acid, maleic acid, and so on.

The quantitative ratio of $Al^{3+}$ to the chelating agent is not particularly limited. The molar ratio with which a stable complex is formed with $Al^{3+}$ is different depending on the kind of chelating agent. However, it is desirable to adjust the addition amount (molar ratio) of the chelating agent so that the whole amount of the added $Al^{3+}$ source is chelated to dissolve $Al^{3-}$. For example, the molar ratio with which the $Al^{3+}$ source and oxalic acid form a stable complex is 1:3, the molar ratio with which the $Al^{3+}$ source and citric acid form a stable complex is 1:2, and the molar ratio with which the $Al^{3+}$ source and EDTA form a stable complex is 1:1.

In addition, as will be described later, it is possible to form the chelated Al from an aluminum compound that is inexpensive and readily available, and the production cost can be reduced as compared with the case that the anthraquinone compounds are used. Particularly when a divalent to tetravalent organic acid that is inexpensive and readily available is used as a chelating agent, the production cost-reducing effect is significant.

[1-2] $Al^{3+}$ Source:

With respect to the chelated Al, the chelated Al itself (namely, $Al^{3+}$ that has already been chelated) may be added to the environment where the sulfate-reducing bacterium exists, or an $Al^{3+}$ source and a chelating agent may also be added to the environment to produce the chelated Al in the environment. Even when the $Al^{3+}$ source and the chelating agent are separately added, the chelated Al is promptly formed in the environment.

The "$Al^{3+}$ source" is a substance capable of producing $Al^{3+}$ that is to be a central ion of a chelate in the presence of water. The specific kind of the substance is not particularly limited. However, it is preferable that the substance is at least one aluminum compound selected from the group consisting of $Al_2O_3$, $AlCl_3$, $Al(OH)_3$, and $Al_2(SO_4)_3$. In addition, the term "at least one" means that the compounds may be used alone or in combination of two or more.

"$Al_2O_3$, $AlCl_3$, $Al(OH)_3$, and $Al_2(SO_4)_3$" include hydrides thereof, not to mention anhydrides thereof. Moreover, these compounds may take a crystalline form or an amorphous form (for example, amorphous alumina and so on). Furthermore, it is not necessary to use a pure substance as one of these compounds, and a mixture may be used. For example, a mineral that contains these compounds can be used as an $Al^{3+}$ source.

[2] Gypsum Composition:

The gypsum composition of the present invention is a gypsum composition comprising gypsum (A) as a main component and contains chelated Al (B) in addition to the gypsum (A), and the chelated Al (B) is contained in a range of 0.01 to 20 mass parts relative to 100 mass parts of the gypsum (A).

[2-1] Gypsum:

The "gypsum" as is referred to in the present invention is a mineral comprising calcium sulfate as a main component and includes a hemihydrate, a dihydrate, an anhydride, and so on of calcium sulfate. Accordingly, the gypsum can be used alone or in combination of two or more of the above-described gypsum. The hemihydrate of calcium sulfate ($CaSO_4 \cdot 1/2H_2O$) is also called hemihydrate gypsum or calcined gypsum. Examples of the hemihydrate of calcium sulfate include β-type hemihydrate gypsum and α-type hemihydrate gypsum.

Moreover, it is preferable in the present invention that a part or the whole of the gypsum is calcined gypsum. The "calcined gypsum" as is referred to in the present invention includes, in addition to the hemihydrate gypsum, anhydrous calcium sulfate ($CaSO_4$, also referred to as soluble anhydrous gypsum or type III anhydrous gypsum) that readily changes to hemihydrate gypsum as a result of absorbing moisture in air.

Accordingly, as calcined gypsum in the present invention, the β-type hemihydrate gypsum, the α-type hemihydrate gypsum, and the type III anhydrous gypsum can be used alone or can be mixed and used in combination of two or more.

Moreover, any of natural products (bassanite and so on), by-product gypsum, and waste gypsum can be used as raw material gypsum for calcined gypsum. However, it is preferable from the standpoints of production cost, recycling promotion, environmental protection, and so on that a part or the whole of the gypsum is calcined gypsum.

[2-2] Chelated Al:

Chelated Al that is the same as the chelated Al already described in the method for performing bacteriostasis of the present invention can be used in the gypsum composition of the present invention. The form of the chelating agent is not particularly limited. However, it is preferable to use a powder chelating agent. Usually, powdered gypsum is used as gypsum that is a main material in the gypsum composition of the present invention. Accordingly, handling becomes easier when a powdered chelating agent is used in the same way as in the above-described gypsum.

The gypsum composition of the present invention contains the chelated Al (B) in a range of 0.01 to 20 mass parts relative to 100 mass parts of the gypsum (A). It is possible to selectively inhibit the proliferation of the sulfate-reducing bacterium to thereby suppress the hydrogen sulfide generation without inhibiting the proliferation of another bacterium by setting the content of the chelated Al to 0.01 mass parts or more. Moreover, the above-described effect can be obtained until the content of the chelated Al reaches 20 mass parts.

However, it is preferable that the chelated Al (B) is contained in a range of 0.1 to 10 mass parts relative to 100 mass parts of the gypsum (A), more preferably 0.2 to 2 mass parts. It is possible to suppress the hydrogen sulfide generation more surely by setting the content of the chelated Al (B) to 0.1 mass parts or more. On the other hand, even though a large amount of chelated Al is added, it does not necessarily mean that the suppression effect is increased in accordance with the added amount. Accordingly, it is possible to prevent the production cost from increasing more than necessary by setting the content of the chelated Al to 10 mass parts or less.

[2-3] $Al^{3+}$ Source:

The gypsum composition of the present invention includes a gypsum composition containing an $Al^{3-}$ source (b-1) and a chelating agent (b-2) in place of the chelated Al (B). Even though the $Al^{3+}$ source and the chelating agent are added separately, the chelated Al is promptly formed in the gypsum composition due to water that is added during the production process or use of the gypsum composition. With respect to the $Al^{3-}$ source and the chelating agent, the same $Al^{3+}$ source and chelating agent as in the method for performing bacteriostasis of the present invention already described.

[3] Gypsum-Based Solidifying Material and Gypsum-Based Building Material:

As already mentioned, the gypsum composition of the present invention contains gypsum and chelated Al in a predetermined ratio. Accordingly, the present invention includes every gypsum composition that satisfies the above-described composition. Namely, the application of the gypsum composition is not limited. For example, a gypsum composition used in the application that does not make use of chemical reaction of gypsum (hydration reaction) is included in the scope of the present invention. The gypsum compositions used in the application that does not make use of the hydration reaction include a line material for drawing white lines to be used in an athletic field or the like, a fertilizer, a rubble-treating material, and so on.

However, the gypsum composition of the present invention can suitably be used for the application that makes use of the hydration reaction of gypsum, and specifically the gypsum composition of the present invention can suitably be used as a gypsum-based solidifying material or a gypsum-based building material. The gypsum-based solidifying material of the present invention is characterized in that the gypsum-based solidifying material contains a gypsum composition of the present invention in which a part or the whole of the gypsum is calcined gypsum. Moreover, the gypsum-based building material of the present invention is characterized in that the gypsum-based building material is obtained by adding water to a gypsum composition of the present invention in which a part or the whole of the gypsum is calcined gypsum, and molding and solidifying the resultant mixture.

The calcined gypsum (hemihydrate gypsum including type III anhydrous gypsum) has a characteristic of readily changing to dihydrate gypsum ($CaSO_4.2H_2O$) through hydration reaction to form a solidified product having a high strength. Accordingly, the gypsum composition of the present invention in which a part or the whole of the gypsum is calcined gypsum can suitably be used as a gypsum-based solidifying material and a gypsum-based building material.

The gypsum-based solidifying material and the gypsum-based building material of the present invention can selectively inhibit the proliferation of the sulfate-reducing bacterium to thereby suppress the hydrogen sulfide generation without inhibiting the proliferation of another bacterium. Moreover, the gypsum-based solidifying material and the gypsum-based building material of the present invention have performance (strength, fire resistance, sound insulation, seismic resistance, and so on) and construction workability which are in no way inferior to those of the conventional gypsum-based solidifying materials and gypsum-based building materials.

The gypsum-based solidifying material may be the one that solidifies the material itself or may be mixed with another material to solidify the whole mixture. Examples of the gypsum-based solidifying material that solidifies the material itself include wet materials (gypsum-based wet paint materials) etc. such as a gypsum plaster (wall-plastering material) and a jointing material (putty) for gypsum plasterboards. Examples of the gypsum-based solidifying material that is mixed with another material to solidify the whole mixture include solidifying materials (gypsum-based soil-improving materials) etc. for soil treatment in order to solidify surplus soil waste from construction, sludge, mud, and so on.

Gypsum-based building materials include a gypsum board, a gypsum block, or the like to be used for ceiling materials, wall materials, flooring materials, and so on. Examples of the gypsum board include a gypsum plasterboard in which a surface of a gypsum board is covered by raw paper for gypsum boards; a glass mat gypsum plasterboard in which a surface of a gypsum board is covered by a glass fiber mat (sheet); and a gypsum board in which a glass fiber mat (sheet) is buried inside (1 to 2 mm inward from the surface). Moreover, the application of the gypsum boards is not limited to structure use. For example, the gypsum boards are also applicable to a functional gypsum board having functionality for cosmetic use, sound absorption use, moisture absorption use, or the like.

[4] Effect of Gypsum Composition of the Present Invention:

The gypsum composition, the gypsum-based solidifying material, and the gypsum-based building material of the present invention exhibit the effect of selectively inhibiting the proliferation of the sulfate-reducing bacterium to thereby suppress the hydrogen sulfide generation without inhibiting the proliferation of another bacterium when these are placed in the environment where the sulfate-reducing bacterium exists.

EXAMPLES

Hereinafter, the present invention will be described in more specifically by Examples and Comparative Examples. However, the present invention is not limited only to the following constitution of each Example. In addition, "parts" and "%" in the following description are based on mass unless otherwise noted.

[1] Examples 1 to 3 and Comparative Example 1

Method for Performing Selective Bacteriostasis

[Preculture]

In Examples and Comparative Example, the following bacterial strains that are representative typestrains were used. *Desulfovibrio vulgaris* DSM 644$^T$ was acquired from DSMZ (DeutscheSammlung von Mikroorganismen und Zellkulturen GmbH) that is The German Type Culture Collection. The other bacteria were acquired from Biological Resource Center, National Institute of Technology and Evaluation. With respect to these bacterial strains, preculture was conducted using culture media designated by the furnishing institutions. The preculture period was set to about 1 week.
(1) Sulfate-reducing bacterium: *Desulfovibrio vulgaris* DSM 644$^T$
(2) Colon bacillus: *Escherichia coli* NBRC 102203$^T$
(3) Butyric acid bacterium: *Clostridium* butyricum NBRC 13949$^T$

[Subculture]

After conducting the preculture, only bacterial cells were recovered, and subculture was conducted for respective bacteria in the culture media each having a composition shown in Table 1 to Table 3. After conducting the subculture, the bacterial cells that were collected and washed were used in Examples and Comparative Example. In addition, "Deionized water/Al aqueous solution" in Tables shows that deionized water was used when the prepared Al aqueous solution had an aluminum concentration of 0 mM and that an Al solution described later was used when the prepared Al solution had an aluminum concentration of 2 mM or 20 mM.

TABLE 1

Culture Medium Composition for *D. vulgaris*

| | |
|---|---|
| Yeast extract | 1.0 g |
| KH$_2$PO$_4$ | 0.5 g |
| NH$_4$Cl | 1.0 g |
| Na$_2$SO$_4$ | 1.0 g |
| CaCl$_2$•2H$_2$O | 0.1 g |
| MgSO$_4$•7H$_2$O | 0.5 g |
| FeSO$_4$•7H$_2$O | 0.5 g |
| Sodium lactate (70%) | 3.0 g |
| Sodium acetate•trihydrate | 2.8 g |
| Sodium thioglycolate | 0.1 g |
| Sodium ascrobate | 0.1 g |
| Deionized water/Al aqueous solution | 1.0 L |
| pH | 7.2-7.6 |

TABLE 2

Culture Medium Composition for *E. coli*

| | |
|---|---|
| Tripton | 5.0 g |
| Yeast extract | 2.5 g |
| NaCl | 5.0 g |
| Sodium thioglycolate | 0.1 g |
| Sodium ascrobate | 0.1 g |
| Deionized water/Al aqueous solution | 1.0 L |
| pH | 6.8-7.2 |

TABLE 3

Culture Medium Composition for *C. Butyricum*

| | |
|---|---|
| Peptone | 3.3 g |
| Soy peptone | 1.0 g |
| Proteose peptone | 3.3 g |
| Digestive serum | 4.5 g |
| Yeast extract | 1.6 g |
| Meat extract | 0.73 g |
| Liver extract | 0.4 g |
| Soluble starch | 1.6 g |
| Glucose | 1.0 g |
| Na$_2$PO$_4$ | 0.83 g |
| NaCl | 1.0 g |
| Sodium thioglycolate | 0.1 g |
| Sodium ascrobate | 0.1 g |
| Deionized water/Al aqueous solution | 1.0 L |
| pH | 6.9-7.4 |

[Preparation of Al Solutions (AlCl$_3$ Aqueous Solutions)]

A predetermined amount of AlCl$_3$.6H$_2$O was added to distilled water, heated and dissolved in an autoclave, and thereafter an appropriate amount of KOH aqueous solution was added thereto to adjust the pH to around 7.0. Thereby, AlCl$_3$ aqueous solutions for addition to culture media having an AlCl$_3$ concentration of 2 mM and 20 mM were respectively prepared. The AlCl$_3$ aqueous solutions were provided for the method of Comparative Example 1.

[Preparation of Al Solutions (Chelated Al Aqueous Solutions)]

A predetermined amount of AlCl$_3$.6H$_2$O was added to distilled water, heated and dissolved in an autoclave, thereafter an equimolar amount of citric acid to AlCl$_3$ in the aqueous solution and water were added to the aqueous solution of AlCl$_3$.6H$_2$O that was heated and dissolved, and the resultant mixture was stirred for 1 hour. Thereafter, an appropriate amount of KOH aqueous solution was added thereto to adjust the pH to around 7.0. Thereby, chelated Al aqueous solutions for addition to culture media having a citric acid/Al chelate concentration of 2 mM and 20 mM were respectively prepared. The chelated Al aqueous solutions were provided for the method of Example 1.

Chelated Al aqueous solutions for addition to culture media having an oxalic acid/Al chelate concentration of 2 mM, and 20 mM were respectively prepared in the same manner as in Example 1 except that an equimolar amount of oxalic acid to AlCl$_3$ in the aqueous solution and water were added to the aqueous solution of AlCl$_3$.6H$_2$O that was heated and dissolved. The chelated Al aqueous solutions were provided for the method of Example 2.

Chelated Al aqueous solutions for addition to culture media having an EDTA/Al chelate concentration of 2 mM, and 20 mM were respectively prepared in the same manner as in Example 1 except that an equimolar amount of EDTA to AlCl$_3$ in the aqueous solution and water were added to the aqueous solution of AlCl$_3$.6H$_2$O that was heated and dissolved. The chelated Al aqueous solutions were provided for the method of Example 3.

[Preparation of Al-Added Culture Media]

Al-added culture media were prepared by adding components of the culture media which are described in Table 1 to Table 3 and to which sterilization treatment had been applied in advance in an autoclave to the $AlCl_3$ aqueous solutions or chelated Al aqueous solutions prepared described previously so as to make the composition ratios as described in Table 1 to Table 3. The Al-added culture media were used after adjusting the pH thereof as described in Table 1 to Table 3 by adding an appropriate amount of KOH and hydrochloric acid.

[Culture]

To a 100 ml (nominal volume) sterilized vial, 100 ml of the Al-added medium was poured, and the inside of the vial was made to be in an anaerobic state by allowing a deoxidized nitrogen gas to blow into the culture medium for a certain period of time. Each subcultured bacterial cell (sulfate-reducing bacterium, colon bacillus, and butyric acid bacterium) was inoculated to the culture medium so that the concentration of the bacterial cell became $10^6$ cells. Thereafter, the vial was sealed with a butyl rubber stopper and an aluminum seal, and shaking culture was conducted in an incubator with a temperature of 37° C. The shaking culture was conducted with a number of shakings (110 times/minute) at which hydroxides were not precipitated. A sample was taken out from the culture solution and used for evaluation.

[Evaluation Method (Measurement of Protein Amount)]

From the vial, 1 ml of the culture medium was collected and suspended in 1 ml of sterile distilled water after removing the culture medium components. Proteins were extracted from the suspension with an ultrasonic crusher, and the protein amount was measured by a BCA method (bicinchoninic acid method). The proliferation-inhibiting effect (bacteriostatic effect) for each bacterial cell was evaluated by the protein amount.

[Results]

Figure 1:
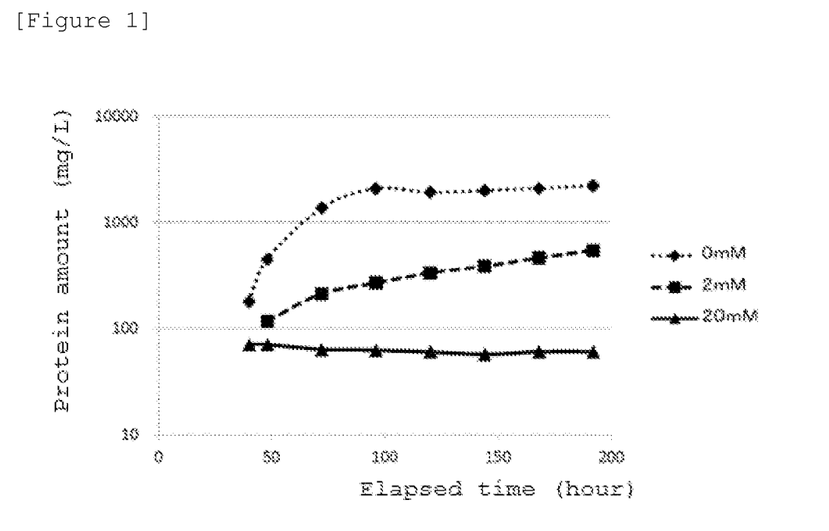
FIG. 1 is a graph showing evaluation results of proliferation-inhibiting effect for a sulfate-reducing bacterium by chelated Al.
Figure 2:
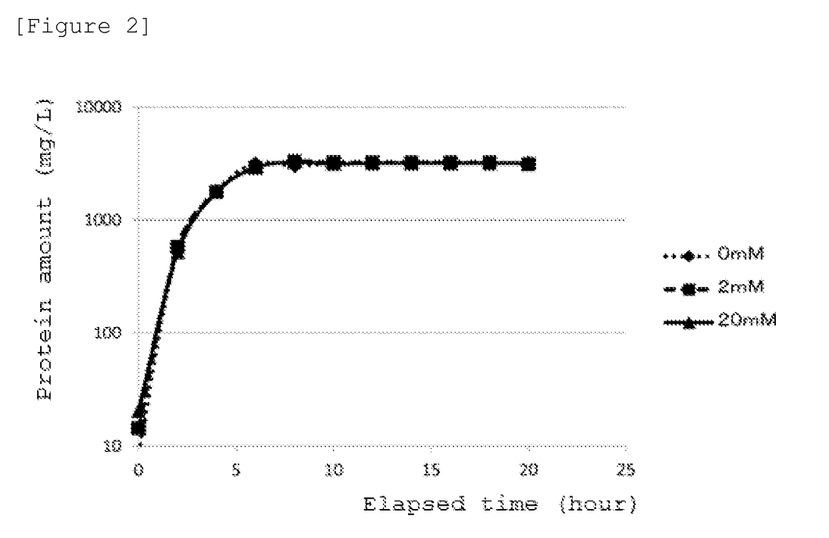
FIG. 2 is a graph showing evaluation results of proliferation-inhibiting effect for a colon bacillus by chelated Al.
Figure 3:
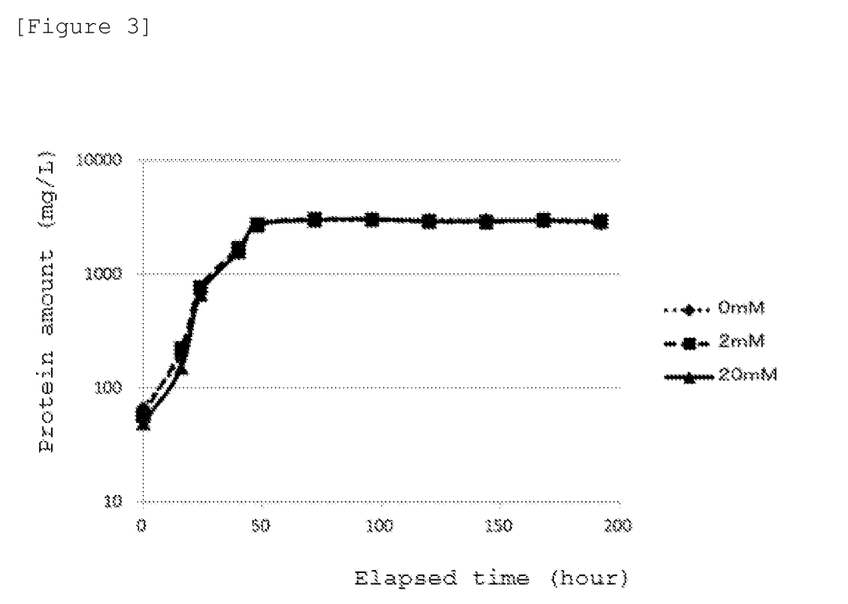
FIG. 3 is a graph showing evaluation results of proliferation-inhibiting effect for a butyric acid bacterium by chelated Al.
Figure 4:
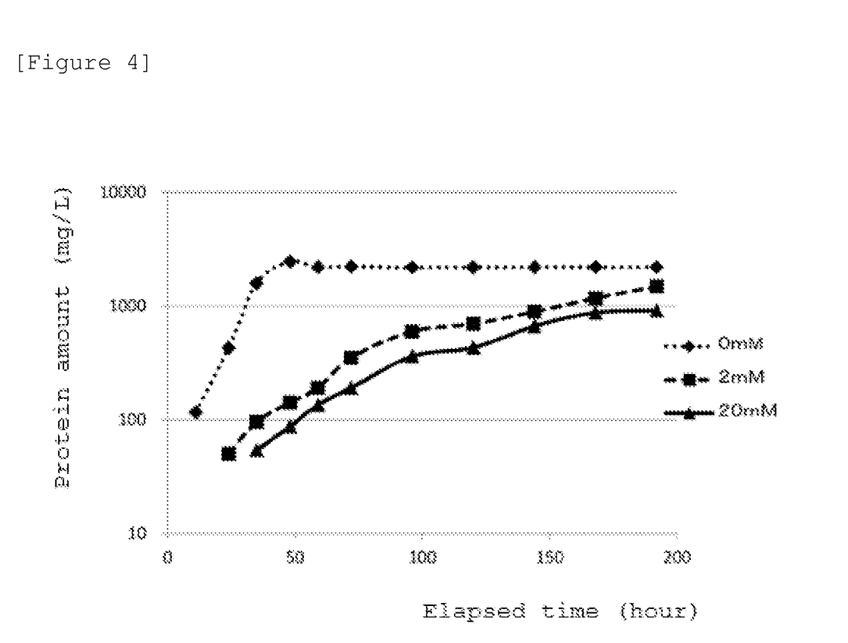
FIG. 4 is a graph showing evaluation results of proliferation-inhibiting effect for a sulfate-reducing bacterium by $AlCl_3$.
Figure 5:
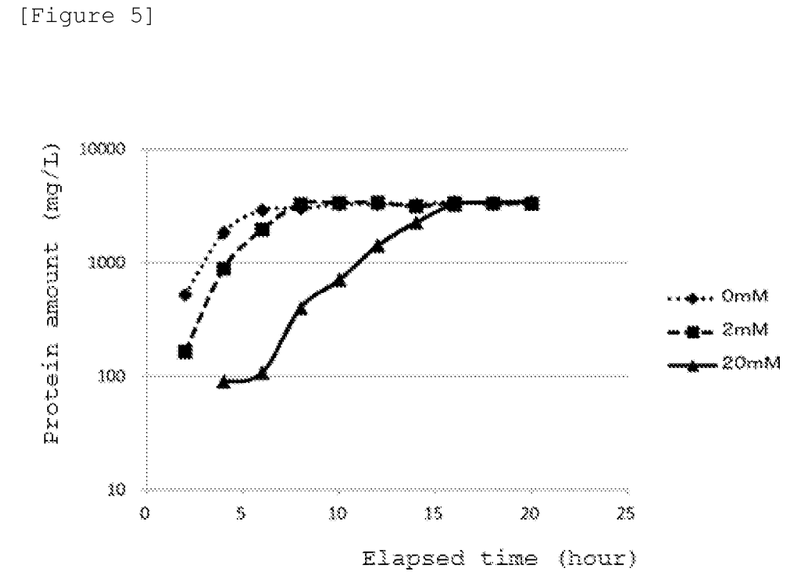
FIG. 5 is a graph showing evaluation results of proliferation-inhibiting effect for a colon bacillus bacterium by $AlCl_3$.
Figure 6:
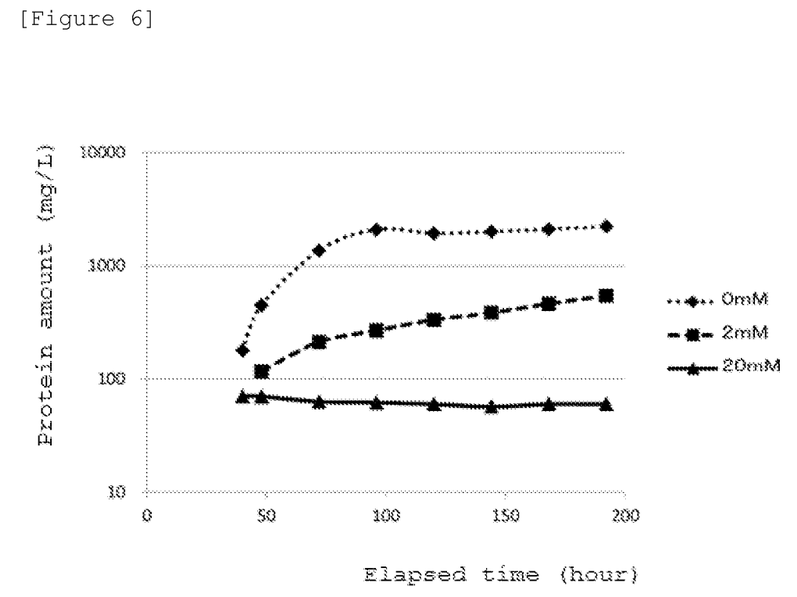
FIG. 6 is a graph showing evaluation results of proliferation-inhibiting effect for a butyric acid bacterium by $AlCl_3$.

With respect to the method of Example 1 (addition of the citric acid/Al chelate), FIG. 1 shows a graph demonstrating a bacteriostatic effect for the sulfate-reducing bacterium, FIG. 2 shows a graph demonstrating a bacteriostatic effect for the colon bacillus, and FIG. 3 shows a graph demonstrating a bacteriostatic effect for the butyric acid bacterium. Moreover, with respect to the method of Comparative Example 1 (addition of $AlCl_3$), FIG. 4 shows a graph demonstrating a bacteriostatic effect for the sulfate-reducing bacterium, FIG. 5 shows a graph demonstrating a bacteriostatic effect for the colon bacillus, and FIG. 6 shows a graph demonstrating a bacteriostatic effect for the butyric acid bacterium. In these graphs, the abscissa denotes elapsed time (unit: hour), and the ordinate denotes the logarithmic value of protein amount (unit: mg/L).

According to the method of Comparative Example 1 (addition of $AlCl_3$), the increase in protein amount is inhibited in all of the culture solutions of the sulfate-reducing bacterium, the colon bacillus, and butyric acid bacterium as shown in FIG. 4 to FIG. 6. Namely, according to the method of Comparative Example 1, not only the proliferation of the sulfate-reducing bacterium but also the proliferation of the colon bacillus and butyric acid bacterium were inhibited.

Moreover, according to the method of Example 1 (addition of the citric acid/Al chelate), the increase in protein amount was inhibited in the culture solution of the sulfate-reducing bacterium as shown in FIG. 1. Namely, the proliferation of the sulfate-reducing bacterium was inhibited.

On the other hand, even when the Al chelate was added, the protein amount was increased in the culture solutions of the colon bacillus and the butyric acid bacterium as shown in FIG. 2 and FIG. 3 in the same way as in the case of not adding the Al chelate. Namely, the proliferation of the colon bacillus and the butyric acid bacterium was not inhibited and the selective bacteriostatic effect was recognized with respect to the method of Example 1. In addition, the same selective bacteriostatic effects as in Example 1 were also recognized with respect to the method of Example 2 (addition of the Al/oxalic acid chelate) and the method of Example 3 (addition of the Al/EDTA chelate), although the effects were not shown in the figures.

[2] Examples 4 to 8, and Comparative Examples 2 and 3

Gypsum Composition

[Preparation of Gypsum Composition]

Gypsum compositions each having a composition described in Table 4 (Example 4 to 8, and Comparative Examples 2 and 3). As the gypsum, calcined gypsum obtained by pulverizing and firing waste gypsum was used. As the aluminum source, $AlCl_3$ was used. As the chelating agent, citric acid was used.

TABLE 4

Composition of Gypsum Composition

| | Composition ratio of gypsum composition (mass parts) | | |
|---|---|---|---|
| | Calcined gypsum | $AlCl_3$ | Citric acid |
| Comparative Example 2 | 100 | — | — |
| Comparative Example 3 | 100 | 0.002 | (Equimolar to $AlCl_3$) |
| Example 4 | 100 | 0.02 | (Equimolar to $AlCl_3$) |
| Example 5 | 100 | 0.2 | (Equimolar to $AlCl_3$) |
| Example 6 | 100 | 2 | (Equimolar to $AlCl_3$) |
| Example 7 | 100 | 10 | (Equimolar to $AlCl_3$) |
| Example 8 | 100 | 20 | (Equimolar to $AlCl_3$) |

Into a 100 ml (nominal volume) sterilized vial, 100 ml of the culture medium described in Table 1 and 2 g of each gypsum composition of Examples 4 to 8 and Comparative Examples 2 and 3 were charged. Furthermore, the pH of the resultant mixture was adjusted to 6.5 by adding an appropriate amount of calcium hydroxide aqueous solution. The pH adjustment was conducted for the purpose of preventing the pH of the culture solution from shifting to an acidic side to thereby create an environment where bacteria cannot live.

Next, the inside of the vial was made to be in an anaerobic state by allowing a deoxidized nitrogen gas to blow into the vial for a certain period of time. Furthermore, the subcultured sulfate-reducing bacterium was inoculated to the culture medium so that the concentration of the bacterial cell became $10^6$ cells. Thereafter, the vial was sealed with a butyl rubber stopper and an aluminum seal, and shaking culture was conducted in an incubator with a temperature of 37° C. for 100 hours. The shaking culture was conducted with a number of shakings (110 times/minute) at which hydroxides were not precipitated. A sample was taken out from the culture solution and used for evaluation. In addition, the culture condition was set so that hydrogen sulfide is easily generated for the purpose of generating hydrogen sulfide. Namely, the culture condition was not intended to reproduce a soil improvement site or a site of illegal dumping or the like.

[Evaluation Method (Measurement of Protein Amount)]

From the vial, 1 ml of the culture medium was collected and suspended in 1 ml of sterile distilled water after removing the culture medium components. Proteins were extracted from the suspension with an ultrasonic crusher, and the protein amount was measured by a BCA method (bicinchoninic acid method). The proliferation-inhibiting effect (bacteriostatic effect) for each bacterial cell was evaluated by the protein amount. The results are shown in Table 5.
[Evaluation Method (Hydrogen Sulfide Generation Amount)]

A culture solution collected from the vial was filtered with a membrane filter having a pore diameter of 0.22 μm, then the filtrate was appropriately diluted with distilled water, and the hydrogen sulfide generation amount was measured by HPLC (High Performance Liquid Chromatography). As HPLC, an HPLC system manufactured by Tosoh Corporation, the HPLC system comprising a pump, a column oven, a column for anion analysis, and a UV detector was used. The results are shown in Table 5.

TABLE 5

Evaluation Results

| | Hydrogen sulfide generation amount (mM) | Protein amount (mg/l) |
|---|---|---|
| Comparative Example 2 | 13 | 2000 |
| Comparative Example 3 | 11 | 1500 |
| Example 4 | 5.5 | 200 |
| Example 5 | 2.7 | 60 |
| Example 6 | 1 | 50 |
| Example 7 | 1 | 50 |
| Example 8 | 1 | 50 |

Regarding the gypsum compositions of Examples 4 to 8, both of the hydrogen sulfide generation amount and the protein amount were remarkably small as compared with those for the gypsum composition of Comparative Example 2 (adding neither $AlCl_3$ nor the Al chelate), and the proliferation of the sulfate-reducing bacterium was inhibited. In addition, it is considered that the reason why the hydrogen sulfide generation amount did not become 0 is because hydrogen sulfide that was dissolved in some amount in the culture solutions was detected. Among others, with the gypsum compositions of Examples 5 to 8 (the Al chelate, 0.2 to 20 mass parts), the hydrogen sulfide generation was able to be suppressed at a sufficient level. Particularly, with the gypsum compositions of Examples 6 to 8 (the Al chelate, 2 to 20 mass parts), the hydrogen sulfide generation was able to be suppressed almost completely.

Moreover, it is considered from the data for the gypsum composition of Example 8 that the addition of 10 mass parts of the Al chelate is enough to sufficiently suppress the hydrogen sulfide generation. Accordingly, it can be said that the gypsum compositions of Examples 4 to 7 (the Al chelate, 0.02 to 10 mass parts) are preferable taking the production cost into consideration. And it can be said that the gypsum composition of Example 5 or 6 (the Al chelate, 0.2 to 2 mass parts) is preferable from the standpoint that the hydrogen sulfide generation can be suppressed almost completely and the gypsum composition can be produced at a low cost.

On the other hand, regarding the gypsum composition of Comparative Example 3 (the Al chelate, 0.002 mass parts), both of the hydrogen sulfide generation amount and the protein amount were small as compared with those of the gypsum composition of Comparative Example 2 (adding neither $AlCl_3$ nor the Al chelate) and it was recognized that the proliferation of the sulfate-reducing bacterium was inhibited. However, the effect was insufficient.

In addition, 100 kg of each gypsum composition of Examples 4 to 8 was added relative to 1 $m^3$ of mud having a water content of 40%, thereafter the resultant mixture was sufficiently kneaded to thereby conduct solidifying treatment. As a result thereof, any of the treatment products was solidified and had a sufficient strength to be bearable to handling. Moreover, it was confirmed that the pH of any treatment product was in a range being evaluated as neutral and having no impact on the environment.

Moreover, when a gypsum plaster (described in JIS A6904), a jointing material for gypsum plasterboards (described in JIS A6914), a gypsum board (described in JIS A6901) and so on were produced from the gypsum compositions, the gypsum compositions of Examples 4 to 8 did not cause any problem in production lines. In addition, the gypsum plaster and the jointing material for gypsum plasterboards are granular gypsum compositions and also gypsum-based solidifying materials that react with water to be hardened. Moreover, the gypsum board is a gypsum-based building material obtained by adding water to the gypsum composition, then forming the resultant mixture into a plate shape, and solidifying the plate-shaped formed body.

Furthermore, it was confirmed that the gypsum compositions of Examples 4 to 8 did not have any adverse effect on the performance and construction workability of the gypsum plaster, the jointing material for gypsum plasterboards, the gypsum board, and so on. Furthermore, when the same tests as in Examples 4 to 8 were conducted using, as samples, the gypsum plasterboards and the gypsum plasters produced from the gypsum compositions of Examples 4 to 8 as raw materials, the hydrogen sulfide generation was clearly suppressed as compared with the conventional gypsum plasterboards and gypsum plasters.

INDUSTRIAL APPLICABILITY

The method for performing bacteriostasis of the present invention can be utilized for inhibiting the proliferation of the sulfate-reducing bacterium and consequently suppressing the hydrogen sulfide generation.

Moreover, the gypsum composition of the present invention can suitably be used as a gypsum composition, a gypsum-based solidifying material, and a gypsum-based building material each capable of suppressing the hydrogen sulfide generation. More specifically, the gypsum composition of the present invention can be utilized as a gypsum-based solidifying material such as a gypsum plaster (wall-plastering material), a jointing material (putty) for gypsum plasterboards, and a gypsum-based soil-improving material (solidifying material for solidifying surplus soil waste from construction, sludge, mud, and so on). Moreover, the gypsum composition of the present invention can be utilized as a gypsum-based building material such as: a gypsum board (including a gypsum plasterboard) such as a ceiling material, a wall material, and a flooring material; a gypsum block; a gypsum board for structure use; and a functional gypsum board (gypsum board having a function for cosmetic use, sound absorption use, moisture absorption use, or the like). Furthermore, the gypsum composition of the present invention can be utilized as another gypsum composition such as a line material for drawing white lines, a fertilizer, and a rubble remover.

The invention claimed is:

1. A method for performing selective bacteriostasis of a sulfate-reducing bacterium, the method comprising: selectively inhibiting proliferation of the sulfate-reducing bacterium by allowing chelated Al to coexist with the sulfate-reducing bacterium in an environment where the sulfate-reducing bacterium exists.

2. The method for performing selective bacteriostasis according to claim 1, wherein the chelated Al is produced in the environment where the sulfate-reducing bacterium exists by adding an $Al^{3+}$ source and a chelating agent in the environment.

3. The method for performing selective bacteriostasis according to claim 2, wherein the $Al^{3+}$ source is at least one Al compound selected from the group consisting of $Al_2O_3$, $AlCl_3$, $Al(OH)_3$, and $Al_2(SO_4)_3$.

4. The method for performing selective bacteriostasis according to claim 1, wherein the sulfate-reducing bacterium is a bacterium living in a middle temperature range from 20 to 45° C. and a neutral pH range from 5 to 9.

5. The method for performing selective bacteriostasis according to claim 2,
   wherein the chelating agent is at least one compound selected from the group consisting of polycarboxylic acids, polyamines, aminopolycarboxylic acids, bipyridines, porphyrins, and crown ethers.

6. The method for performing selective bacteriostasis according to claim 2,
   wherein the chelating agent is at least one compound selected from the group consisting of oxalic acid, malonic acid, tartaric acid, glutaric acid, malic acid, citric acid, maleic acid, ethylene diamine, ethylenediaminetetraacetic acid, 2,2'-bipyridine, 1,10-phenathroline, and 18-crown-6.

* * * * *